United States Patent [19]
Wheeler

[11] Patent Number: 6,050,982
[45] Date of Patent: Apr. 18, 2000

[54] CONCEALED COLOSTOMY APPARATUS AND METHOD

[76] Inventor: Alton D. Wheeler, 3940 Fox Meadow La., Pasadena, Tex. 77504

[21] Appl. No.: 08/963,347

[22] Filed: Nov. 3, 1997

[51] Int. Cl.[7] ................................ A61F 5/44; A61F 2/00; A61F 2/02
[52] U.S. Cl. .......................... 604/332; 604/337; 600/29; 600/32
[58] Field of Search ................... 604/332, 333, 604/334, 335, 336, 337, 338, 339, 340, 341, 342, 343, 344, 345; 600/29, 30, 31, 32

[56] References Cited

U.S. PATENT DOCUMENTS

| | | | |
|---|---|---|---|
| 2,243,529 | 5/1941 | Grossman et al. | 600/32 |
| 2,341,984 | 2/1944 | Graves | 604/332 |
| 2,667,167 | 1/1954 | Raiche | 604/339 |
| 3,718,141 | 2/1973 | Goetz | 128/283 |
| 4,210,131 | 7/1980 | Perlin | 128/1 |
| 4,941,869 | 7/1990 | D'Amico | 600/32 |
| 4,950,223 | 8/1990 | Silvanov | 600/32 |
| 5,261,898 | 11/1993 | Polin et al. | 604/328 |
| 5,785,677 | 7/1998 | Auweiler | 604/28 |

FOREIGN PATENT DOCUMENTS 0168967  1/1986  European Pat. Off. ............... 604/332

*Primary Examiner*—Robert A. Clarke
*Assistant Examiner*—Miley Craig Peppers, III
*Attorney, Agent, or Firm*—William W. Haefliger

[57] ABSTRACT

A concealed colostomy apparatus comprising a sleeve insertible into the bowel via a discharge opening thereof for retention therein, the sleeve then having a discharge end; a cap removably interfitting the discharge end of the sleeve; and a flexible pouch received in collapsed position into the sleeve to in turn receive feces from the bowel, the cap being removable to allow distending of the pouch outside the sleeve and continued filling of fecal matter into the pouch.

14 Claims, 6 Drawing Sheets

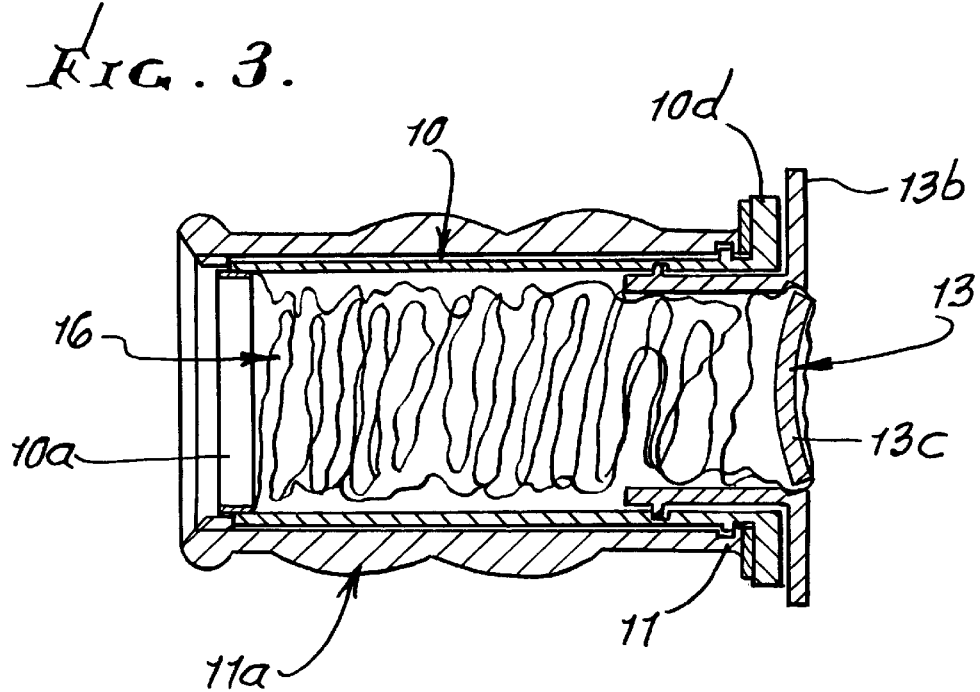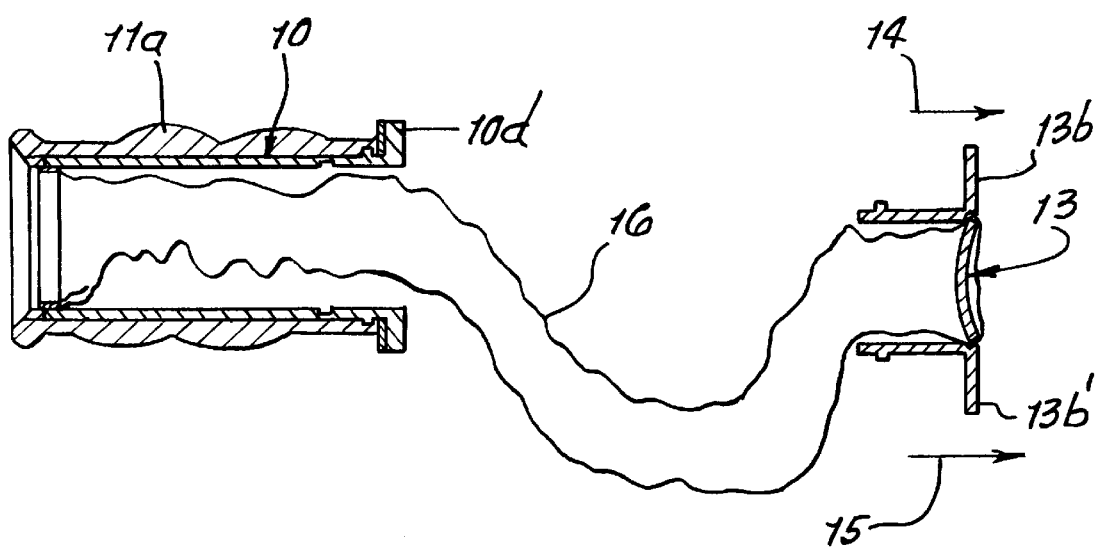

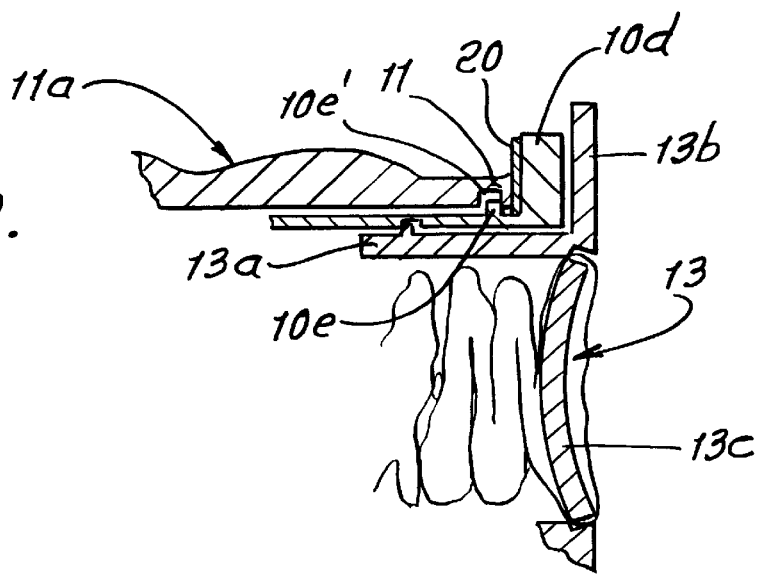
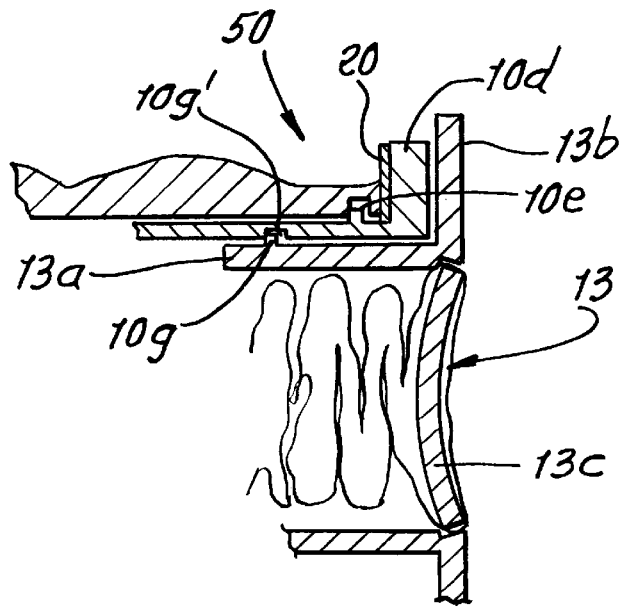
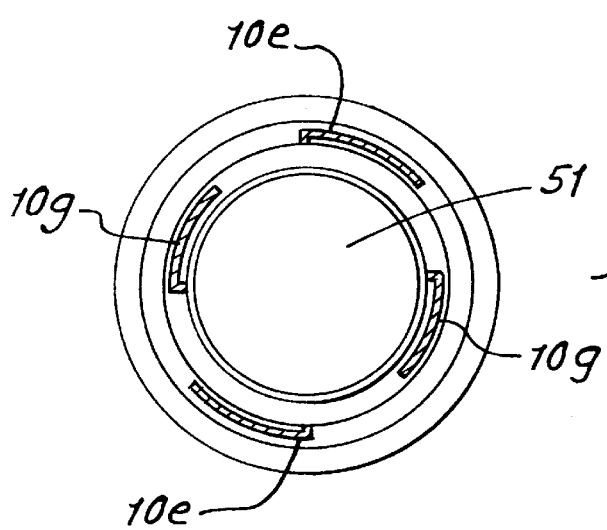

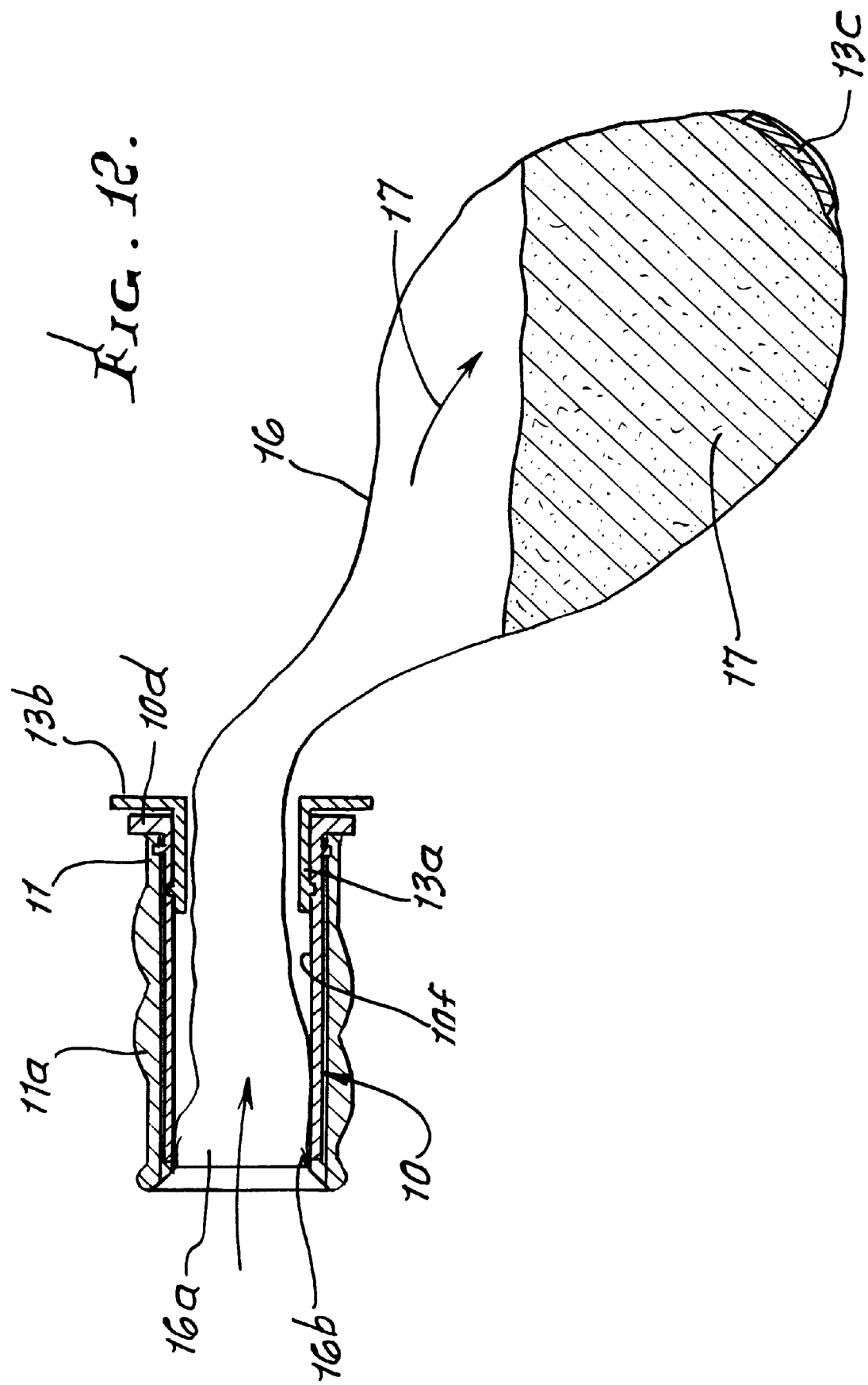

CONCEALED COLOSTOMY APPARATUS AND METHOD

BACKGROUND OF THE INVENTION

This invention relates generally to colostomy, and more particularly, to improved colostomy apparatus and its method of use.

There is continual need for improvements in colostomy techniques and apparatus; and in particularly, there is great need for simplified and reliable apparatus, which is unobtrusive in its application to the colon and its method of use.

SUMMARY OF THE INVENTION

It is a major object of the invention to provide improved apparatus and method meeting the above need. Basically, the concealed colostomy apparatus of the invention comprises:

a) a sleeve insertible into the lower bowel via a discharge opening thereof for retention therein, the sleeve then having a discharge end, b) a cap removably interfitting the discharge end of the sleeve, c) and a flexible pouch received in collapsed position into the sleeve to in turn receive feces from the bowel, the cap being removable to allow distending of the pouch outside the sleeve and continued filling of fecal matter into the pouch.

It is another object of the invention to provide a cap, as referred to, which has a tubular portion receivable in telescopic interfitting relation with the sleeve.

As will be seen, the cap tubular portion may be received in retained relation into the sleeve. Further, the cap may have a grip flange seating against the discharge end of the sleeve.

It is a further object of the invention to provide a sleeve, as referred to, and the lower end of which defines a sleeve flange that seats the cap flange, to limit pouch reception in collapsed condition into the sleeve, and in position for in-filling. In this regard, the sleeve may have open-end communication to or communication with the discharge opening of the lower bowel.

An additional object is to provide for cap attachment to the collapsed pouch in such manner as to allow distending of the pouch as the cap is removed away from the sleeve.

A yet further object of the invention is to provide an anchor of the sleeve to the pouch at the entrance end thereof, and adapted to be received into the bowel via the sleeve.

Other objects include provision of an installation tool and of flushing means.

The method of the invention includes the steps:

a) providing a sleeve and inserting the sleeve into the lower bowel via a discharge opening thereof for retention therein, the sleeve then having a discharge end, b) providing a cap removably interfitting the discharge end of the sleeve, c) and providing a flexible pouch and receiving the pouch in collapsed position into the sleeve to in turn receive feces from the bowel, the cap being removable to allow distending of the pouch outside the sleeve and continued filling of fecal matter into the pouch.

These and other objects and advantages of the invention, as well as the details of an illustrative embodiment, will be more fully understood from the following specification and drawings, in which:

DRAWING DESCRIPTION

FIG. 3 is like FIG. 2 showing installation in the bowel;

FIG. 4 is a view like FIG. 3 but showing cap removal and distending of the pouch outside the sleeve;

FIG. 9 is a fragmentary section showing flange-to-flange attachment;

FIG. 10 is an enlarged view showing a connection; and

FIG. 11 is an end view of the flange connection.

FIG. 12 is a view like FIG. 4 but showing infilling of feces into the distended pouch, with a plug inserted into sleeve.

DETAILED DESCRIPTION

Figure 1:
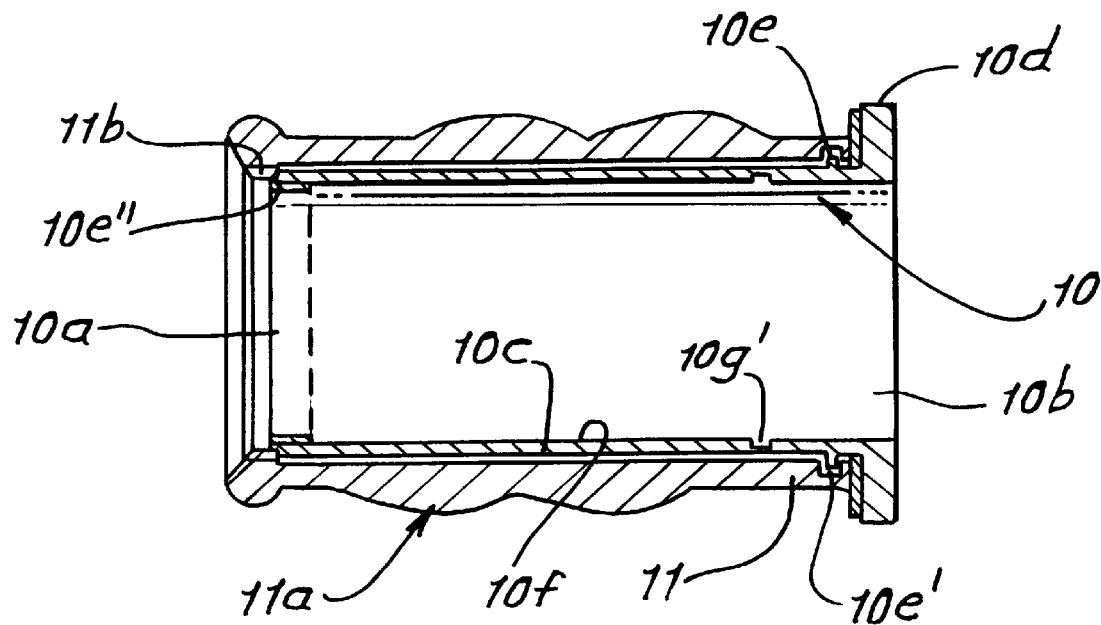
FIG. 1 is an axial section taken through a sleeve incorporating the invention.

In FIG. 1, a sleeve 10 is shown inserted into a discharge opening 11 of the bowel 11a for retention therein. The sleeve 10 has an entrance end 10a, a discharge end 10b, a thin, tubular side wall 10c, and a small seating flange 10d about end 10b. The sleeve may consist of plastic (synthetic resin) material. Sleeve 10 has a tang 10e that presses into the bowel at 10e' at the bowel discharge opening. The left end 10e" seals against bowel lip 11b'.

Figure 7:
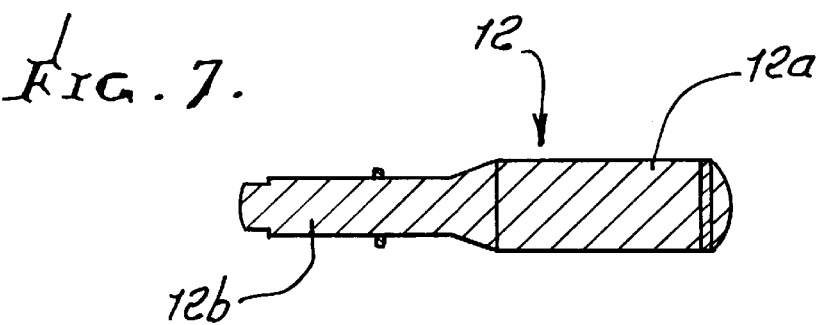
FIG. 7 is an elevation showing an installation tool.

Tool 12, seen in FIG. 7, may be employed to insert the sleeve. The tool has a handle 12a, and a reduced diameter stem 12b receivable into the sleeve, to advance the sleeve into the bowel opening.

Figure 2:
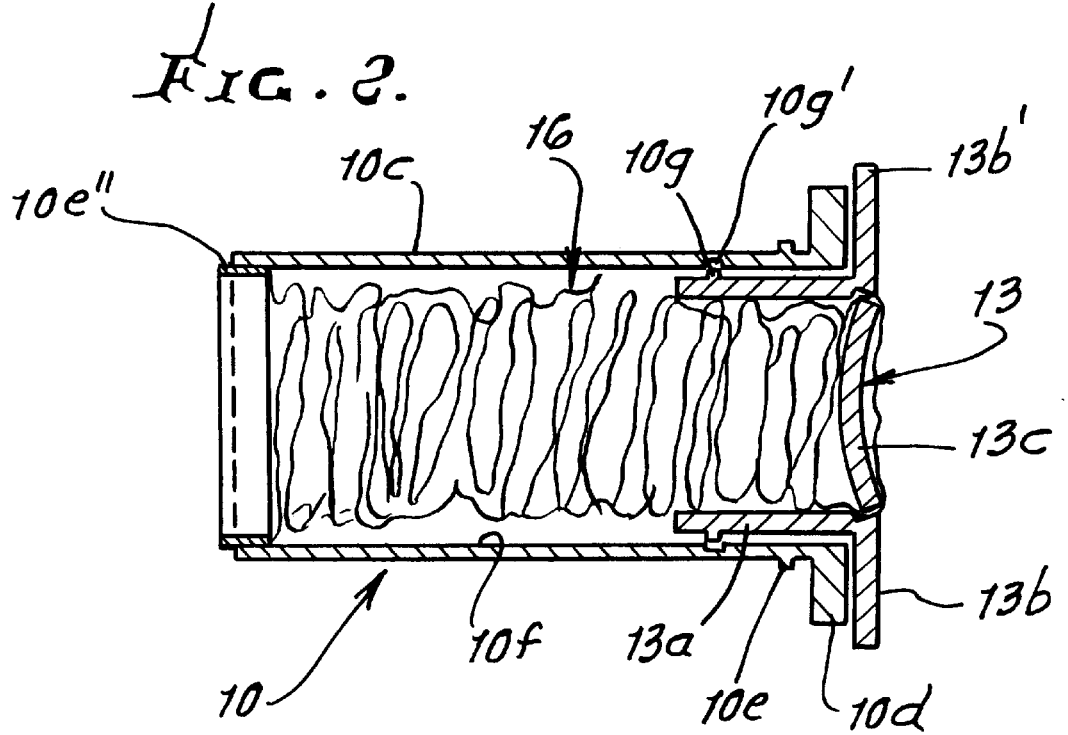
FIG. 2 is a view like FIG. 1 but showing a pouch and a cap assembled to the sleeve.

FIGS. 2 and 3 show provision of a cap or stopper 13, to close the sleeve at its discharge end. The cap has a stem 13a frictionally received into, and retained to, the sleeve bore 10f, to close that bore, and a flange 13b receivable against the seating flange 10d to seat against that flange and seal off therebetween. The cap flange has a lip 13b' extending outwardly of the seating flange 10d, to provide a finger grip for exerting force to pull the cap out of and away from the sleeve, as seen in FIG. 4, and without finger pulling of flange 10d. Fingers appear at 14 and 15. A tang 10g provides removable attachment of the cap stem 13a to groove 10g' may be provided, as better seen in FIG. 10, to resist feces pressure push out of the cap. Soft seal 20 between 10d and 11 serves as an odor barrier.

Figure 5:
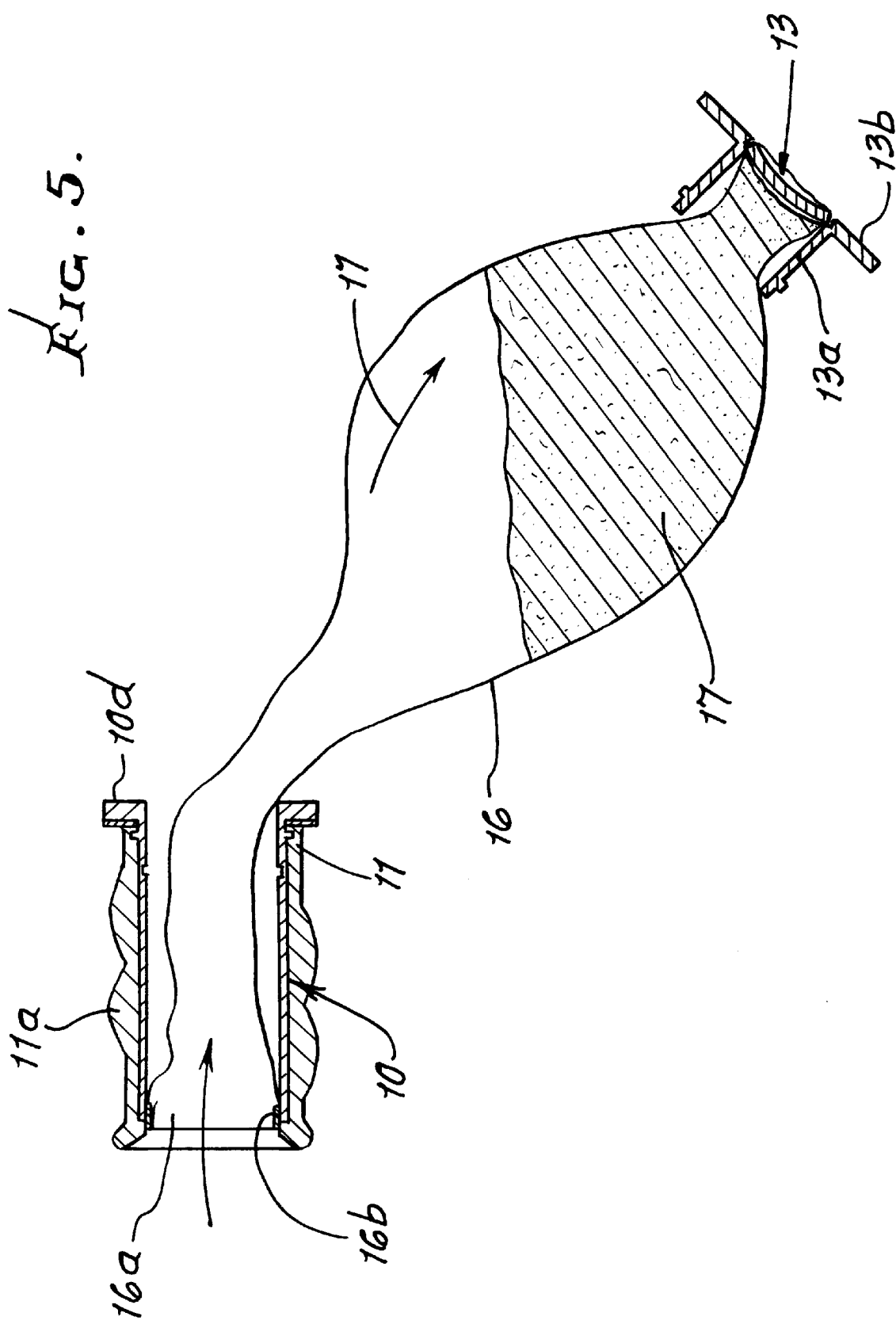
FIG. 5 is a view like FIG. 4 but showing in-filling of feces into the distended pouch.
Figure 6:
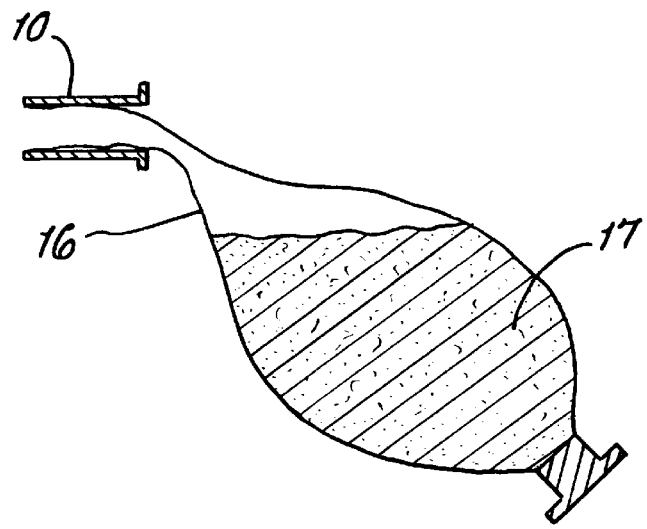
FIG. 6 is like FIG. 5 but showing removal of the sleeve and pouch entrance end from the bowel.

A flexible, flaccid pouch 16 is received in collapsed position into the sleeve to in turn receive feces 17 from the bowel via the sleeve, as during distension of the pouch outside the bowel, as indicated in FIGS. 4 and 5. The pouch has an open entrance end 16a, within the sleeve, the pouch entrance lip 16b attached annularly to the sleeve, as near its entrance end, as shown. The user, having sensed need for elimination, may remove the cap and distend the pouch for in-filling, whereby the cap and pouch may be concealed prior to that felt need. The closed, distal end of the pouch is attached to the cap, for distension. A pouch retainer plug 13c fits into an opening in the cap 13. It is convex toward the bowel interior, but allows over center deflection to the right to release the pouch in an emergency, due to pressure build-up and blow-out (gas or feces). See FIG. 12 showing plug 13d concave toward the pouch.

Figure 8:
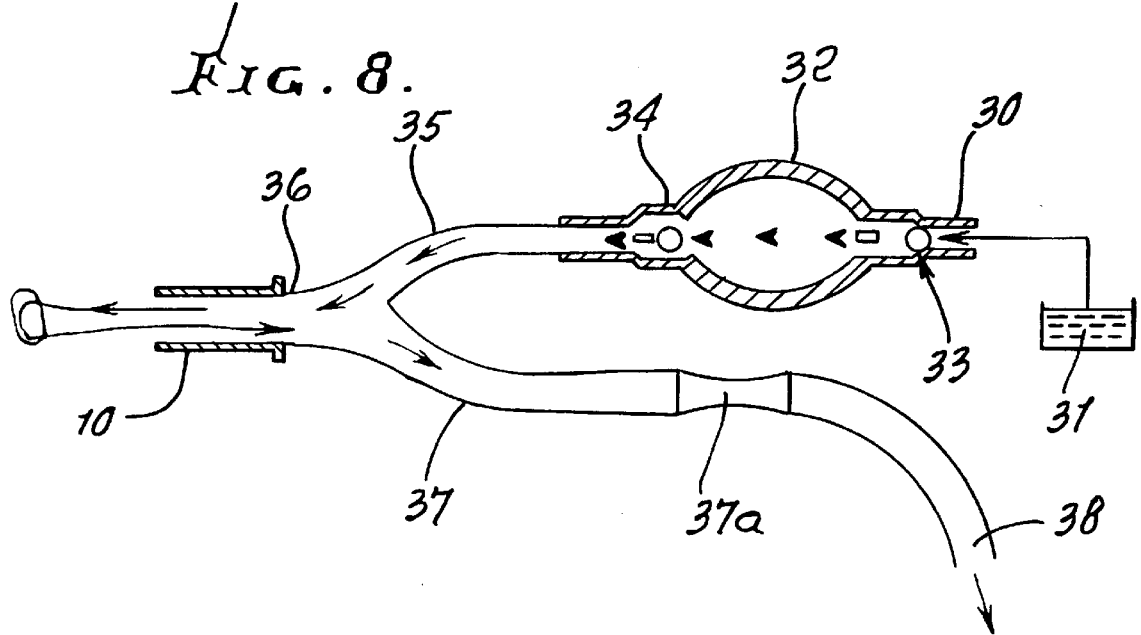
FIG. 8 is a schematic diagram showing a flushing method and means.

FIG. 8 shows a method and means to flush the sleeve, while inserted into the lower bowel. A duct 30 leads from a flush water source 31 to a squeeze pump in the form of a flexible, rubber bulb 32, via an entrance check valve 33. Expansion of the bulb draws water into its interior via valve 33. Squeezing of the bulb discharges liquid via a discharge check valve 34 to a duct 35. That duct has a terminal 36 receivable into the sleeve 10, as shown. A discharge duct 37 leads from terminal 36 to a manual squeeze valve 37*a*, and to a discharge opening 38. Bulb 32 may be squeezed, while valve 37 is manipulated to allow pressure flushing of the sleeve followed by gravity discharge via duct 37.

Further features are listed as follows:

1. The receptacle or sleeve may be manufactured of alumina ceramic transcutaneous or comparable material to prevent skin exit site infections about the stoma. The receptacle sleeve is locked onto the installation tool and inserted into the existing stoma and turned clockwise, while applying slight inward pressure until the edge is flush with the skin surface. See the attachment at 50 in FIG. 10. Local anesthetic may be required.

2. The disposable hidden colostomy pouch capsule may be made of a medically approved plastic housing and a thin membrane pouch. The open end of the pouch is attached to the end of the capsule housing. A cap (or button) 51 is attached to the closed end of the pouch. The button may lock in a housing groove. The pouch capsule is inserted into the stoma receptacle, and rotated ¼ turn to lock in place.

3. The colon can be emptied when the sensation of pressure occurs or by predetermined timing. This is done by turning the button counterclockwise and extending the pouch, allowing it to fill. The capsule housing button is then removed to remove the colostomy pouch unit for discard.

I claim:

1. In concealed colostomy apparatus, the combination comprising:
    a) a sleeve insertible into a bowel via a discharge opening thereof for retention therein, the sleeve then having a discharge end,
    b) a cap removably interfitting the discharge end of the sleeve,
    c) and a flexible pouch received in collapsed position into the sleeve to in turn receive feces from the bowel, the cap being removable to allow distending of the pouch outside the sleeve and continued filling of fecal matter into the pouch.

2. The combination of claim 1 wherein the cap has a tubular portion receivable in telescopic interfitting relation with the sleeve.

3. The combination of claim 2 wherein the cap tubular portion is received in retained relation into the sleeve.

4. The combination of claim 3 wherein the cap has a grip flange seating against the discharge end of the sleeve.

5. The combination of claim 4 wherein the discharge end of the sleeve defines a sleeve flange that seats said cap flange.

6. The combination of claim 2 wherein the cap has a grip flange seating against the discharge end of the sleeve.

7. The combination of claim 6 wherein the discharge end of the sleeve defines a sleeve flange that seats said cap flange.

8. The combination of claim 7 including a means to removably retain the sleeve flange to the cap flange.

9. The combination of claim 8 wherein said means comprises hook and fastener assembly.

10. The combination of claim 1 wherein the sleeve has open-end communication with a discharge opening of a lower bowel.

11. The combination of claim 1 wherein said cap is attached to said collapsed pouch to allow distending of the pouch as the cap is removed away from the sleeve.

12. In the method of using concealed colostomy apparatus, the steps that include:
    a) providing a sleeve and inserting the sleeve into a lower bowel via a discharge opening thereof for retention therein, the sleeve then having a discharge end,
    b) providing a cap removably interfitting the discharge end of the sleeve,
    c) and providing a flexible pouch and receiving the pouch in collapsed position into the sleeve to in turn receive feces from the bowel, the cap being removable to allow distending of the pouch outside the sleeve and continued filling of fecal matter into the pouch.

13. The method of claim 12 including distending the pouch from the sleeve for feces in-filling, after first removing the cap from the sleeve.

14. The method of claim 13 including thereafter removing the sleeve from the lower bowel, for disposal.

* * * * *